United States Patent [19]

Stokker

[11] 4,308,378

[45] Dec. 29, 1981

[54] CIS/TRANS ISOMERIZATION OF 6-(SUBSTITUTED-ARYL-ETHENYL)-3,4,5,6-TETRAHYDRO-4-HYDROXY-2H-PYRAN-2-ONES

[75] Inventor: Gerald E. Stokker, Gwynedd Valley, Pa.

[73] Assignee: Merck & Co., Inc., Rahway, N.J.

[21] Appl. No.: 183,661

[22] Filed: Sep. 2, 1980

[51] Int. Cl.³ .......................................... C07D 309/32
[52] U.S. Cl. .................................. 542/441; 424/279; 542/429
[58] Field of Search .......................... 542/441, 429

[56] References Cited

U.S. PATENT DOCUMENTS

| | | | |
|---|---|---|---|
| 3,522,245 | 7/1970 | Brinkhoff | 542/441 |
| 3,600,403 | 8/1971 | Brinkhoff | 542/441 |
| 4,198,425 | 4/1980 | Mitsui et al. | 260/343.5 |

FOREIGN PATENT DOCUMENTS

| | | |
|---|---|---|
| 867421 | 11/1978 | Belgium . |
| 10951 | 6/1980 | European Pat. Off. . |

*Primary Examiner*—Arthur P. Demers
*Attorney, Agent, or Firm*—William H. Nicholson; Mario A. Monaco

[57] ABSTRACT

Biologically inactive cis-6-(substituted-arylethenyl)-3,4,5,6-tetrahydro-4-hydroxy-2H-pyran-2-ones are isomerized to the corresponding anti-hypercholesterolemic trans-isomers by heating in the presence of a heavy metal salt.

6 Claims, No Drawings

CIS/TRANS ISOMERIZATION OF 6-(SUBSTITUTED-ARYL-ETHENYL)-3,4,5,6-TETRAHYDRO-4-HYDROXY-2H-PYRAN-2-ONES

BACKGROUND OF THE INVENTION

This invention is concerned with a novel process for converting biologically inactive cis-6-(substituted-arylethenyl)-3,4,5,6-tetrahydro-4-hydroxy-2H-pyran-2-ones to the anti-hypercholesterolemic trans-isomers by heating the cis-isomer with a heavy metal or salt thereof.

Belgian Pat. No. 867,421 discloses a group of synthetic compounds of the generic formula:

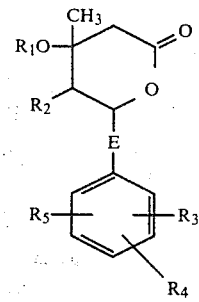

in which E represents a direct bond, a $C_{1-3}$ alkylene bridge or a vinylene bridge and the various R's represent a variety of substituents, which are anti-hypercholesterolemic agents by virtue of their ability to specifically inhibit HMG-CoA reductase, the enzyme which catalyzes the rate-limiting step in the biosynthesis of cholesterol.

Willard et al., U.S. Application Ser. No. 140,323, filed Apr. 14, 1980, now abandoned, discloses related compounds of generic structure:

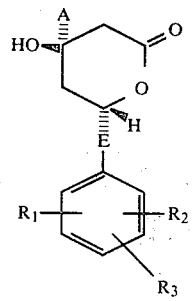

wherein A is hydrogen or methyl, E is a direct bond, a $C_{1-3}$ alkylene bridge or a vinylene bridge and the R's represent a variety of substituents. The active stereoisomer is that depicted which is a 4-R-trans-isomer.

As with most synthetic procedures, the process employed by Willard et al., is not stereo-specific but ends up with a cis/trans-mixture, the components of which must be separated to produce the useful trans-isomer in a pure state and a similar quantity of the up to now, useless, cis-isomer.

Now with the present invention there is provided a novel process for converting these inactive cis-6-(substituted-arylethenyl)-3,4,5,6-tetrahydro-4-hydroxy-2H-pyran-2-ones to the biologically active trans-isomer. After isolating the trans-isomer from the resulting cis/trans-mixture, the remaining cis-isomer is recycled in the novel isomerization process of this invention.

DETAILED DESCRIPTION OF THE INVENTION

The novel process of this invention comprises isomerization of the cis-compound, I, to the trans-compound, II,

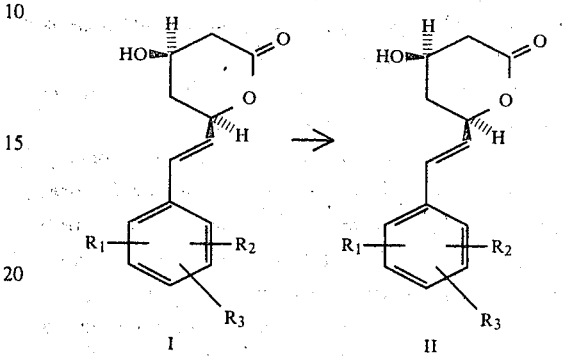

wherein
$R_1$, $R_2$ and $R_3$ are each selected from
(a) hydrogen,
(b) halogen,
(c) $C_{1-4}$ alkyl,
(d) $C_{1-4}$ haloalkyl,
(e) phenyl,
(f) phenyl substituted by
  (1) halogen,
  (2) $C_{1-4}$ alkoxy,
  (3) $C_{2-8}$ alkanoyloxy,
  (4) $C_{1-4}$ alkyl, or
  (5) $C_{1-4}$ haloalkyl, and
(g) $OR_4$ in which $R_4$ is
  (1) hydrogen,
  (2) $C_{2-8}$ alkanoyl,
  (3) benzoyl,
  (4) phenyl,
  (5) halophenyl,
  (6) phenyl $C_{1-3}$ alkyl,
  (7) $C_{1-9}$ alkyl,
  (8) cinnamyl,
  (9) $C_{1-4}$ haloalkyl,
  (10) allyl,
  (11) cycloalkyl-$C_{1-3}$ alkyl,
  (12) adamantyl-$C_{1-3}$ alkyl, or
  (13) substituted phenyl-$C_{1-3}$ alkyl in each of which the substituents are selected from
    (i) halogen,
    (ii) $C_{1-4}$ alkoxy,
    (iii) $C_{1-4}$ alkyl, or
    (iv) $C_{1-4}$ haloalkyl.

It is preferred that $R_1$, $R_2$, and $R_3$ are each selected from
(a) halogen,
(b) $C_{1-4}$ alkyl,
(c) $C_{1-4}$ haloalkyl,
(d) phenyl or substituted phenyl in which the substituent is
  (1) halogen,
  (2) $C_{1-4}$ alkyl,
  (3) $C_{1-4}$ alkoxy, and
(e) $OR_4$ in which $R_4$ is
  (1) phenyl, (2) halophenyl, or (3) substituted phenyl-$C_{1-3}$ alkyl wherein the substituents are selected from (i) halogen, and (ii) $C_{1-4}$ haloalkyl.

It is most preferred that:

$R_1$ is in the 6-position and is halophenyloxy, halophenylalkoxy or halophenyl, especially where halo is fluoro or chloro; and $R_2$ and $R_3$ are halo, especially chloro, in the 2 and 4-positions.

The compounds in which $R_1$ is halophenyl, espcially fluorophenyl and chlorophenyl, are especially preferred. The isomerization is accomplished by heating the cis-isomer, Compound I, in an aqueous inert organic solvent in the presence of a heavy metal salt.

The isomerization proceeds at temperatures above about 50° C. up to temperatures at which the starting material and/or product is subject to decomposition. Temperatures below 200° C. are recommended, especially about 75° C. to about 125° C., and conveniently at the reflux temperature of the solvent mixture.

The isomerization is continued until further heating does not increase the content of the desired trans-isomer in the reaction mixture. The actual time required depends on the temperature and other factors and varies from 40 to 100 hours, and usually about 60 to 76 hours.

The aqueous, inert, organic solvent is composed of water and a non-hydroxylic organic solvent in which the starting material is soluble such as acetonitrile, dioxane, tetrahydrofuran, or the like, especially acetonitrile. The water and organic solvent are present in a ratio within the range of 1:1 to 1.10 (V:V), preferably about 1:5.

The heavy metal salt useful in the novel process of this invention is a salt derived from a heavy metal cation such as the cations of any valence state of mercury, zinc, lead, or cadmium, and an anion such as bromide, chloride, fluoride, iodide, nitrate or sulfate. The preferred salt is mercuric chloride. In the reaction, the amount of heavy metal salt is approximately equal, on a molar basis, to the amount of starting material.

The resulting trans-isomer is isolated from the reaction mixture by standard extraction and chromatographic techniques, especially as described by Willard et al. in Ser. No. 140,323, filed Apr. 14, 1980 and as described in the Examples of this invention that follow.

The preparation of the starting materials for the process of this invention is also described by Willard et al., in Ser. No. 140,323, filed Apr, 14, 1980, the disclosure of which is incorporated herein by reference, as illustrated in the following flow sheets and other information extracted from the Willard et al. application.

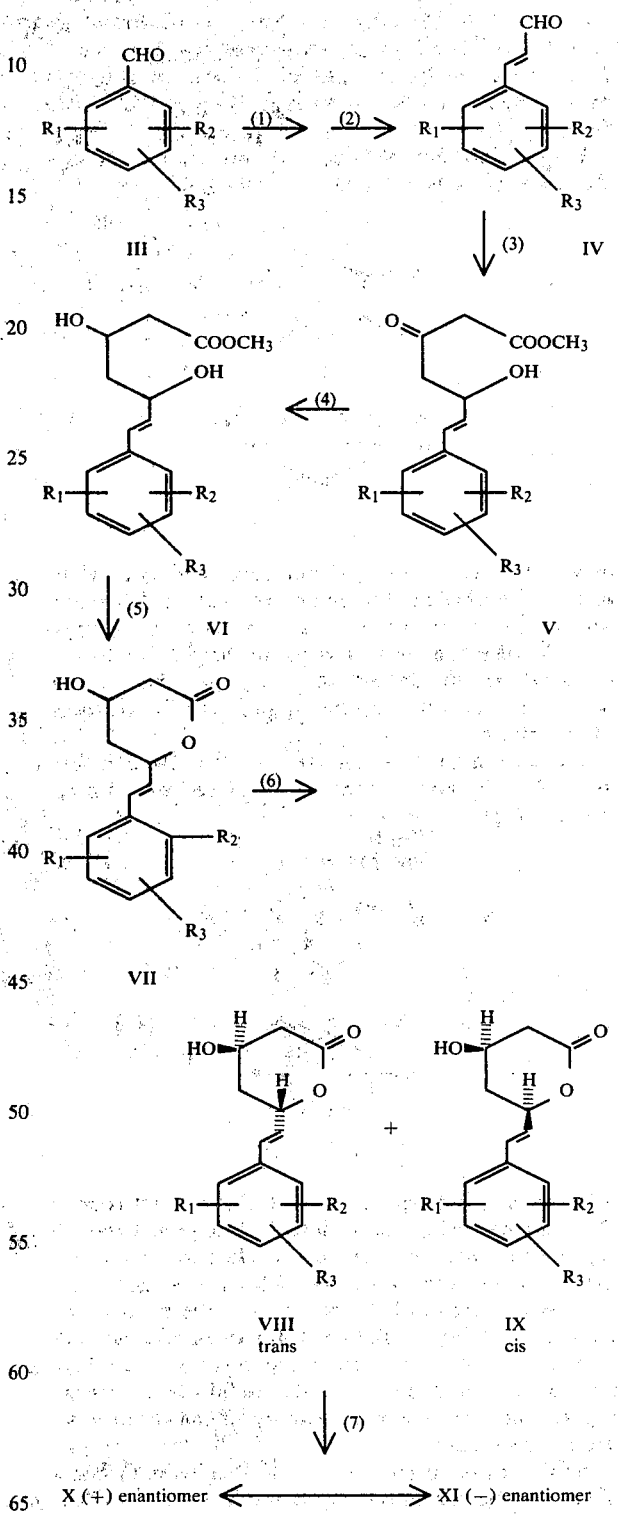

FLOW SHEET I

SYNTHESIS OF VINYLENE BRIDGED COMPOUNDS

DEFINITIONS: $R_1$, $R_2$ and $R_3$ are as defined in specification for Formulas I and II.

FLOW SHEET II
SYNTHESIS OF 6-[2-(6-PHENYLPHENYL)ETHENYL]PYRANONES
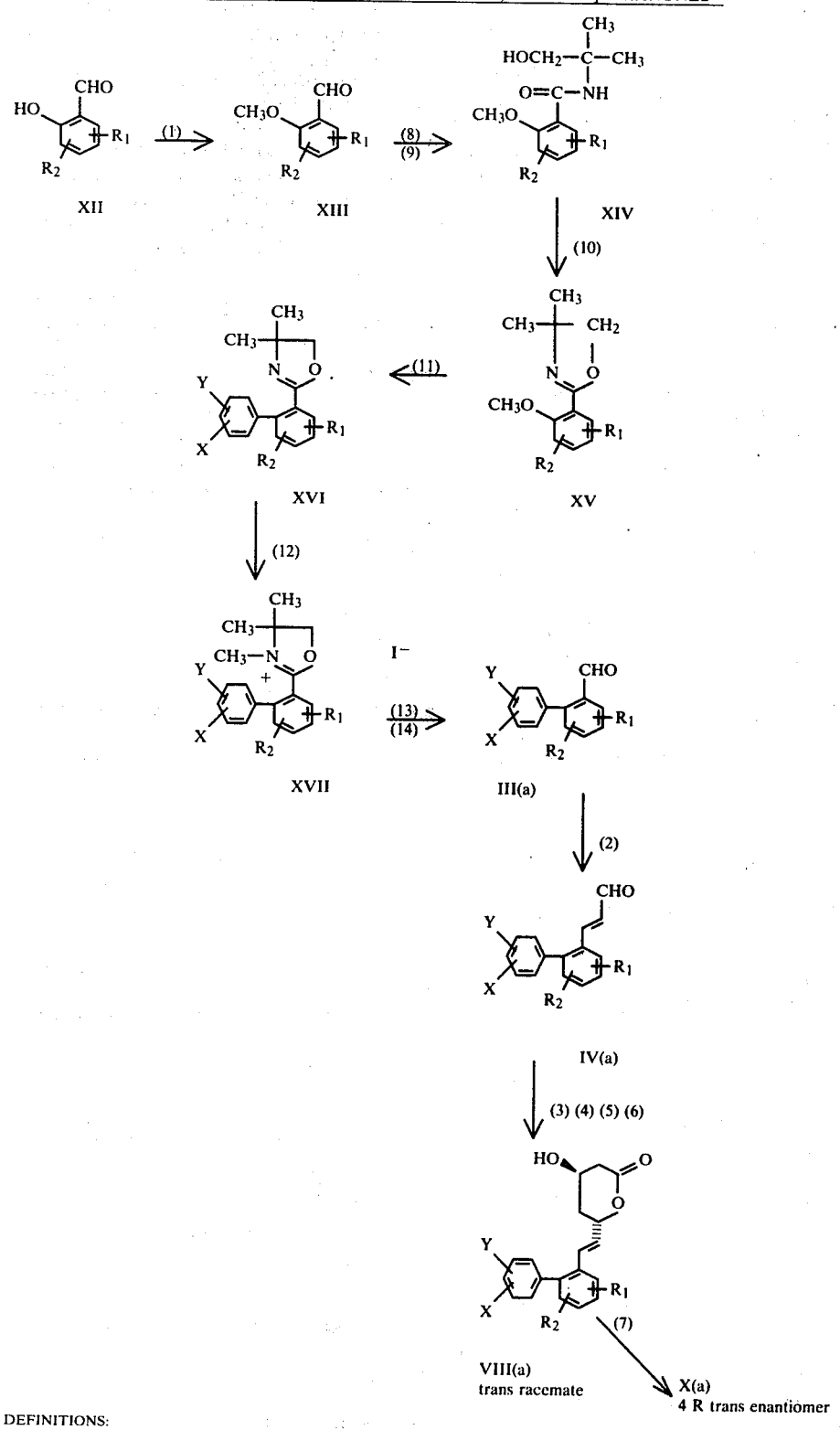
VIII(a) trans racemate
X(a) 4 R trans enantiomer
DEFINITIONS:
$R_1$ and $R_2$ are as defined in the specification for Formulas I and II. X and Y are halogen, $C_{1-4}$ alkyl or $C_{1-4}$ alkoxy.
III(a), IV(a), VIII(a) and X are the special variants here of the general compounds in Flow Sheet I.

FLOW SHEET III
ALTERNATE PREPARATION OF BENZALDEHYDES III(a)

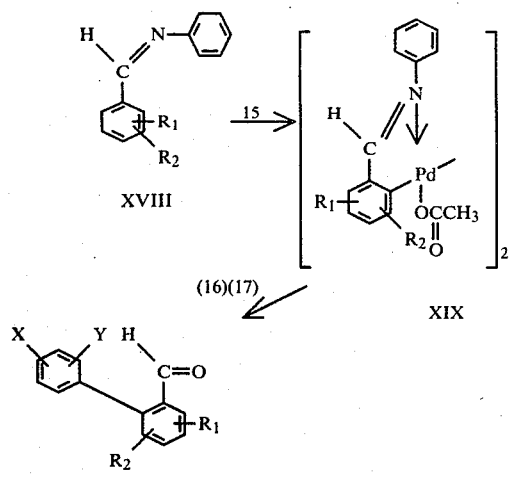

III(a)

DEFINITIONS:
$R_1$ and $R_2$ are as defined in the specification for Formulas I and II.
X and Y are halogen, $C_{1-4}$ alkoxy or $C_{1-4}$ alkyl.

REACTIONS IN FLOW SHEETS

1. When $R_1$, $R_2$ or $R_3$ is HO- or bears a hydroxyl substituent, the HO- group is etherified using a reagent $R_4X$ in a suitable solvent such as DMF and the like in the presence of a suitable base, preferably an alkali metal carbonate such as $K_2CO_3$, to give the corresponding ether $R_4O-$ which can be carried through the remainder of the synthesis. If it is desired to remove $R_4$ at a later synthetic step, $R_4$ is chosen as an easily removable group such as $CH_3OCH_2CH_2OCH_2-$ (the MEM protecting group). The MEM group is removed readily by treatment with a Lewis acid catalyst such as $ZnBr_2$ in a suitable solvent such as $CH_2Cl_2$ and the like. When the starting material is devoid of a hydroxyl group, step (1) is omitted.

2. Aldol Reaction. This can be run in several ways:

(a) The classical Aldol synthesis in which acetaldehyde is condensed with the starting benzaldehyde, the resulting β-hydroxyaldehyde is acetylated with acetic anhydride and acetic acid is eliminated thermally to give the corresponding cinnamaldehyde.

(b) The directed Aldol condensation in which the anion of an appropriately N-substituted ethylidenylimine, such as ethylidenecyclohexylimine and the like, is condensed with the starting benzaldehyde at or below room temperature in an aprotic solvent, such as THF and the like, to afford a β-hydroxy-β-phenylpropylidenylimine which, upon concomitant dehydration and imine hydrolysis in an acidic medium, such as dilute aqueous HCl, provides the corresponding cinnamaldehyde.

(c) The use of a nucleophilic acetaldehyde equivalent in which cis-2-ethoxyvinyllithium, generated from cis-1-ethoxy-2-tri-n-butylstannylethylene, is condensed with the starting benzaldehyde to give an allylic alcohol which is subsequently rearranged, under suitable acidic conditions, to the corresponding cinnamaldehyde.

(3) Dianion Step. Reaction with the dianion of acetoacetic ester in a suitable aprotic solvent such as THF, dioxane and the like.

(4) Reduction with $NaBH_4$ in a suitable solvent such as methanol, ethanol and the like at or below room temperature.

(5) Lactonization. Saponification by base (e.g. NaOH) in aqueous alcohol followed by acification and cyclodehydration by heating in toluene. NOTE: Steps 3, 4 and 5 are usually carried out sequentially without purification of compounds V and VI.

(6) Separation of the cis and trans racemic mixtures by chromatography on silica gel or crystallization.

(7) Resolution of the trans racemate into its enantiomers by treating the (±)-trans lactone with either d-(+) or l-(−)-α-methylbenzylamine to give the diastereomeric dihydroxy amides which are separated by chromatography or crystallization. Hydrolysis of each pure diastereomeric amide under basic conditions, such as ethanolic aOH and the like, affords the corresponding enantiomerically pure dihydroxy acid which, upon lactonization, e.g., in refluxing toluene, provides the pure (+)-trans or (−)-trans enantiomer. Stereochemistry depends on the absolute stereochemistry of the diastereomeric amide from which it is derived.

(8) Treatment with N-bromosuccinimide in $CCl_4$ with irradiation by a sun lamp (*Tetrahedron Letters*, 3809 (1979)).

(9) Treatment with two equivalents of the amine

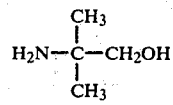

(10) Reaction with $SOCl_2$, (*J. Org. Chem.*, 43, 1372 (1978)).

(11) Reaction with a substituted phenyl Gridnard reagent

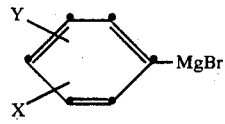

(12) Reaction with methyl iodide in a suitable solvent such as acetone.

(13) Reaction with $NaBH_4$ in a suitable solvent such as ethanol or methanol.

(14) Heating with acid (*J. Het. Chem.*, 3, 531 (1966)).

(15) Reaction with Palladium (II) acetate in acetic acid at reflux.

(16) Reaction with a substituted Grignard reagent

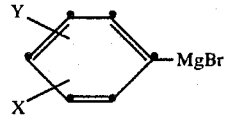

in suitable solvents such as benzene or toluene in the presence of triphenylphosphine.

(17) Hydrolysis with 6 N HCl at ambient temperature.

The products of the novel process of this invention are employed in a pharmaceutical composition consisting of at least one of the compounds of formula II in association with a pharmaceutical vehicle or diluent. The pharmaceutical composition can be formulated in a classical manner utilizing solid or liquid vehicles or diluents and pharmaceutical additives of a type appropriate to the mode of desired administration. The compounds can be administered by an oral route, for example, in the form of tablets, capsules, granules or powders, or they can be administered by a parenteral route in the form of injectable preparations. The dose to be administered depends on the unitary dose, the symptoms, and the age and the body weight of the patient. A dose for adults is preferably between 200 and 2,000 mg per day, which can be administered in a single dose or in the form of individual doses from 1–4 times per day.

A typical capsule for oral administration contains active ingredient (250 mg), lactose (75 mg) and magnesium stearate (15 mg). The mixture is passed through a 60 mesh sieve and packed into a No. 1 gelatin capsule.

A typical injectible preparation is produced by aseptically placing 250 mg of sterile active ingredient into a vial, aseptically freezedrying and sealing. For use, the contents of the vial are mixed with 2 ml of physiological saline, to produce an injectible preparation.

The compounds of this invention also have useful antifungal activities. For example, they may be used to control strains of Penicillium sp., *Aspergillus niger*, Cladosporium sp., *Cochliobolus miyabeanus* and *Hilminthosporium cynodnotis*. For those utilities they are admixed with suitable formulating agents, powders, emulsifying agents or solvents such as aqueous ethanol and sprayed or dusted on the plants to be protected.

Preparation of
(E)-6-[2-(2,4-dichloro-6-phenylmethoxyphenyl)ethenyl]-3,4,5,6-tetrahydro-4-hydroxy2H-pyran-2-one Step A. Preparation of
2,4-Dichloro-6-phenylmethoxybenzaldehyde Potassium carbonate (9.4 g, 67.8 mmole) was added to a stirred solution of 4,6-dichlorosalicylaldehyde (10.8 g, 56.5 mmole) in dimethylformamide (80 ml). The resulting mixture was stirred at 60° for 30 minutes and treated with benzyl bromide (10.6 g, 62.1 mmole). This mixture was stirred one hour at 60° C. and then poured into ice water (1000 ml) to give the title compound (15.9 g, 100%) which melted at 98°–100° C. after recrystallization from hexane. pmr (CDCl$_3$) δ5.10 (2H, s), 7.33 (5H, s), 10.40 (H, s).

Analysis Calc. for C$_{14}$H$_{10}$Cl$_2$O$_2$: Calc.: C, 59.81; H, 3.58. Found: C, 59.98; H, 3.58.

Step B. Preparation of
(E)-2,4-Dichloro-6-phenylmethoxycinnamaldehyde

A stirred suspension of 2,4-dichloro-6-phenylmethoxybenzaldehyde (15.5 g, 55.1 mmole) in acetaldehyde (30 ml) was cooled to 5° C. and treated with 25% methanolic potassium hydroxide (1.4 ml, 6.24 mmole) at such a rate that the internal temperature was maintained at 25°–30° C. The resulting solution was stirred for 30 minutes in the ice bath, treated with acetic anhydride (30 ml) and then heated at 100° C. for 30 minutes. After cooling to 30° C. the solution was treated with water (84 ml) and 12 N hydrochloric acid (7 ml). The resulting mixture was refluxed for 30 minutes and then cooled in an ice bath to give a gummy solid which was recrystallized from cyclohexane to give the title compound (5.6 g, 33%), mp 109°–112° C.: pmr (CDCl$_3$) δ5.10 (2H, s), 7.33 (5H, s), 9.68 (H, d).

Analysis Calc. for C$_{16}$H$_{12}$Cl$_2$O$_2$: Calc.: C, 62.56; H, 3.94. Found: C, 62.66; H, 3.98.

Alternate Step B. Preparation of
(E)-2,4-Dichloro-6-phenylmethoxycinnamaldehyde

A 1.6 M solution (18.8 ml, 30 mmole) of n-butyllithium in hexane was added cautiously to a stirred solution of freshly distilled diisopropylamine (3.0 g, 30 mmole) in anhydrous tetrahydrofuran (200 ml) maintained at 0° C. under a nitrogen atmosphere. The resulting solution was stirred at 0° C. for 15 minutes and then treated with ethylidenecyclohexylamine (3.75 g, 30 mmole). The solution was stirred 15 minutes at 0° C., cooled to −78° C. and treated with a solution of 2,4-dichloro-6-phenylmethoxybenzaldehyde (8.4 g, 30 mmole) in anhydrous tetrahydrofuran (50 ml). The resulting red solution was stirred at −78° C. for 15 minutes and then at 25° C. for 60 minutes. The reaction solution was treated with water (200 ml) and extracted with ether (3×200 ml). The organic extracts were combined, washed with brine (3×100 ml), dried over magnesium sulfate and filtered. The filtrate was evaporated in vacuo, leaving the desired intermediate hydroxyimine as a brown viscous oil (12.5 g): pmr (CDCl$_3$) δ5.10 (2H, s), 5.50 (H, t), 7.37 (5H, s), 7.70 (H, s).

A solution of the oily imine (12.5 g) in tetrahydrofuran (110 ml) was treated with a solution of oxalic acid dihydrate (11 g, 87.2 mmole) in water (22 ml). The resulting solution was refluxed for 30 minutes, cooled to 25° C. and poured into water (500 ml). The resulting mixture was extracted with ether (3×200 ml). The organic extracts were combined, washed with brine (3×50 ml), dried over magnesium sulfate and filtered. The filtrate was evaporated in vacuo, leaving the title compound as a tan solid. The title compound was purified by recrystallization from cyclohexane to give yellow needles (4.7 g, 51%) melting at 109°–111° C.: pmr (CDCl$_3$) δ5.11 (2H, s), 7.33 (5H, s), 9.68 (H, d).

Alternate to Alternate Step B. Preparation of
(E)-2,4-Dichloro-6-phenylmethoxycinnamaldehyde A 1.37 M solution (24.1 ml, 33 mmole) of n-butyllithium in hexane was added cautiously to a stirred solution of cis-1-ethoxy-2-tri-n-butylstannylethylene (11.9 g, 33 mmole) in anhydrous tetrahydrofuran (75 ml) maintained at −78° C. under a nitrogen atmosphere. The resulting solution was stirred at −78° C. for one hour and then treated with a solution of 2,4-dichloro-6-phenylmethoxybenzaldehyde (8.4 g, 30 mmole) in anhydrous tetrahydrofuran (50 ml). The resulting brown solution was stirred at −78° C. for one hour and then allowed to warm to 20° C. The reaction solution was quenched with saturated aqueous sodium bicarbonate (25 ml), diluted with water (100 ml) and then extracted with ether (2×200 ml). The organic extracts were combined, washed with brine (2×100 ml), dried over magnesium sulfate and filtered. The filtrate was evaporated in vacuo, leaving the desired intermediate allylic alcohol as a yellow oil.

The oil was chromatographed on a silica column (400 g) to cause allylic rearrangement to the desired product. Elution with methylene chloride (200 ml) provided a forerun containing tetrabutyltin which was discarded. Continued elution with methylene chloride/methanol (98:2, V:V; 1500 ml) gave the title compound as a pale yellow solid, mp 109°–111° C. (6.4 g, 70%).

Step C. Preparation of Methyl (E)-7-(2,4-dichloro-6-phenylmethoxyphenyl)-5-hydroxy-3-oxo-6-heptenoate Methyl acetoacetate (9.56 g, 82.3 mmole) was added dropwise to a stirred suspension of sodium hydride (50% oil suspension) (3.95 g, 82.3 mmole) in anhydrous tetrahydrofuran at 0° C. under a nitrogen atmosphere. The resulting solution was stirred 15 minutes at 0° C. and then treated with a 1.6 M solution (51.5 ml, 82.3 mmole) of n-butyllithium in hexane over 5 minutes. The resulting yellow solution was stirred 15 minutes at 0° C. and then treated with a solution of (E)-2,4-dichloro-6-phenylmethoxycinnamaldehyde (25.3 g, 82.3 mmole) in anhydrous tetrahydrofuran (150 ml). The resulting orange solution was stirred 15 minutes at 0° C. and then quenched by dropwise addition of 12 N hydrochloric acid (ca. 20 ml). The reaction mixture was diluted with water (100 ml) and extracted with ether ($3 \times 300$ ml). The organic extracts were combined, washed with brine ($3 \times 100$ ml), dried over magnesium sulfate and filtered. The filtrate was evaporated in vacuo leaving the title compound as a yellow oil (34.8 g, 100%): pmr (CDCl$_3$) δ2.75 (2H, d), 3.45 (2H, s), 3.72 (3H, s), 4.71 (H, m), 5.50 (2H, s), 7.37 (5H, s).

Step D. Preparation of Methyl (E)-7-(2,4-Dichloro-6-phenylmethoxyphenyl)-3,5-dihydroxy-6-heptenoate Sodium tetrahydridoborate (1.55 g, 41.1 mmole) was added with stirring to a cooled solution (5° C.) of methyl (E)-7-(2,4-dichloro-6-phenylmethoxyphenyl)-5-hydroxy-3-oxo-6-heptenoate (34.8 g, 82.3 mmole) in ethanol (200 ml) at a rate sufficient to maintain the internal temperature at 15°–20° C. The resulting solution was stirred with ice-bath cooling for 15 min. and then acidified with 6 N hydrochloric acid. The resulting mixture was diluted with water (500 ml) and extracted with ether ($3 \times 250$ ml). The organic extracts were combined, washed with brine ($4 \times 100$ ml), dried over magnesium sulfate and filtered. The filtrate was evaporated in vacuo, leaving the title compound as a yellow oil (34.8 g, 99.5%): pmr CDCl$_3$ δ2.45 (2H, d), 3.65 (3H, s), 4.18 (H, m), 4.45 (H, m), 4.98 (2H, s), 7.28 (5H, s).

Step E. Preparation of (E)-7-(2,4-Dichloro-6-phenylmethoxyphenyl)-3,5-dihydroxy-6-heptenoic acid A solution of methyl (E)-7-(2,4-dichloro-6-phenylmethoxyphenyl)-3,5-dihydroxy-6-heptenoate (34.8 g, 81.8 mmole), 1 N sodium hydroxide (82 ml, 82 mmole) and ethanol (200 ml) was stirred at 25° C. for 15 min. The reaction solution was acidified with 6 N hydrochloric acid, diluted with water (400 ml) and extracted with ether ($3 \times 200$ ml). The combined organic extracts were washed with brine ($3 \times 100$ ml), dried over magnesium sulfate and filtered. The filtrate was evaporated in vacuo, leaving the title compound as an orange oil (33.3 g, 99%); pmr (CDCl$_3$) δ2.47 (2H, d), 4.30 (2H, br m), 4.98 (2H, s), 7.30 (5H, s).

Step F. Preparation of (E)-6-[2-(2,4-Dichloro-6-phenylmethoxyphenyl)ethenyl]-3,4,5,6tetrahydro-4-hydroxy-2H-pyran-2-one A solution of (E)-7-(2,4-dichlorophenylmethoxyphenyl)-3,5-dihydroxy-6-heptenoic acid (33.3 g, 81.3 mmole) in toluene (300 ml) was heated at reflux in a Dean-Stark apparatus. After 2 hours at Dean-Stark apparatus was replaced with a soxhlet containing 3 A molecular sieves (100 g). The solution was refluxed for an additional 4 hours and then the toluene was removed in vacuo leaving a yellow oil (31.7 g) which is a mixture of cis and trans isomers of the title compound. The oil was chromatographed on a silica gel column (900 g). Elution with methylene chlorideacetone (9:1, V:V; 4000 ml) provided a forerun which was discarded. Continued elution with the same eluant (500 ml) gave the trans isomer of the title compound as a pale yellow solid (5.8 g).

Further elution of the column with the same eluant (3250 ml) gave a tan solid (8.8 g), which is a mixture of the cis and trans isomers of the title compound. This cis/trans mixture was chromatographed using a Waters Prep LC500. Separation of this mixture was accomplished by using two prep PAK-500/silica cartridges in series and eluting with methylene chloride-acetone (9:1, V:V). Using the shave recycle technique, the cis (4.7 g) and the trans (3.3 g) isomers of the title compound were obtained. The fractions of the trans isomer, collected from the two chromatographic procedures were combined and recrystallized from n-butyl chloride to give the trans isomer of the title compound (7.3 g, 23%), mp 130°–131° C.: pmr (CDCl$_3$) δ2.64 (2H, m), 4.30 (H, m), 5.07 (2H, s), 5.30 (H, m), 7.42 (5H, s).

Analysis Calc. for $C_{20}H_{18}Cl_2O_4$: Calc.: C, 61.08; H, 4.61. Found: C, 61.12; H, 4.60.

The cis isomer (4.3 g, 13%) of the title compound melted at 130°–131.5° C. after recrystallization from n-butyl chloride: pmr (CDCl$_3$) δ4.30 (H, m), 4.83 (H, m), 5.12 (2H, s), 7.47 (5H, s).

Analysis Calc. for $C_{20}H_{18}Cl_2O_4$: Calc.: C, 61.08; H, 4.61. Found: C, 61.55; H, 4.63

Step G. Preparation and Separation of Diastereomeric Amides

A solution of (±)trans-(E)-6-[2-(2,4-dichlorophenyl)ethenyl]-3,4,5,6-tetrahydro-4-hydroxy-2H-pyran-2-one (2.87 g, 10 mmole) in d-(+)α-methylbenzylamine (15 ml) was stirred for 18 hours at 25° C. and then poured into water (100 ml). This aqueous mixture was acidified with 6 N hydrochloric acid and then extracted with ether ($3 \times 100$ ml). The ether extracts were combined, washed with brine ($4 \times 75$ ml), dried over magnesium sulfate and filtered. Evaporation of the filtrate in vacuo gave the intermediate diastereomeric amides as a tan viscous oil (4.1 g).

The tan viscous oil (3.1 g, 7.6 mmole) was chromatographed on a silica gel column (200 g). Elution with acetone-methylene chloride (1:4, V:V, 1200 ml) gave a forerun which was discarded. Continued elution with the same eluant (1000 ml) gave the diastereomeric amides as a viscous oil (3.0 g).

The diastereomeric amides were separated by chromatography on a Waters Prep LC500. The separation was accomplished by using two prep PAK-500 silica cartridges in series and eluting with acetonemethylene chloride (1:4, V:V). By using the shaverecycle technique isomer A (1.36 g) and isomer B (1.20 g) were obtained.

Recrystallization of isomer A from n-butyl chloride gave colorless clusters (1.0 g) which melted at 106°–108° C., pmr (CDCl$_3$) δ1.47 (3H, d), 2.33 (2H, d), 4.30 (1H, m), 5.17 (1H, q), 7.33 (8H, m).

Analysis Calc. for $C_{21}H_{23}Cl_2NO_3$: Calc.: C, 61.77; H, 5.68; N, 3.43. Found: C, 61.78; H, 5.78; N, 3.50.

Recrystallization of isomer B from n-butyl chloride-petroleum ether gave a pale yellow solid which melted at 55°–60° C., pmr (CDCl$_3$) δ1.47 (3H, d), 2.33 (2H, d), 4.30 (1H, m), 5.17 (1H, q), 7.33 (8H, m).

Analysis Calc. for C$_{21}$H$_{23}$Cl$_2$NO$_3$: Calc.: C, 61.77; H, 5.68; N, 3.43. Found: C, 61.41; H, 5.87; N, 3.30.

Step H. Preparation of (+)trans-(E)-6-[2-(2,4-Dichlorophenyl)ethenyl]-3,4,5,6-tetrahydro-4-hydroxy-2H-pyran-2-one Isomer A (0.74 g, 1.8 mmole) of Step G was dissolved in 95% ethanol (25 ml) containing 1 N sodium hydroxide (3.6 ml, 3.6 mmole) and the solution was refluxed for 54 hours. The ethanol was removed in vacuo and the residue was suspended in water (100 ml) and acidified with 6 N hydrochloric acid. This aqueous mixture was extracted with ether (3×75 ml). The ether extracts were combined, washed with brine (2×50 ml), dried over magnesium sulfate, and filtered. The filtrate was evaporated in vacuo leaving the intermediate acid as a yellow oil (0.54 g).

A solution of the yellow oil in toluene (150 ml) was refluxed through a soxhlet containing molecular sieves (3 Å) for 5 hours. The solution was evaporated in vacuo leaving the (+)trans isomer as a yellow solid. The title compound was purified by recrystallization from ether and then n-butyl chloride to give white needles (0.11 g, 20%) melting at 114°–115° C., pmr (CDCl$_3$) δ2.03 (2H, m), 2.73 (2H, m), 4.46 (1H, m), 5.41 (1H, m), 6.19 (1H, dd) 7.01 (1H, d), 7.14–7.50 (3H, m).

Analysis Calc. for C$_{13}$H$_{12}$Cl$_2$O$_3$: Calc.: C, 54.37; H, 4.21. Found: C, 54.51; H, 4.32.

$[\alpha]_D^{25} = +5.9$ (C, 0.425, chloroform)

Step I. Preparation of (−)trans-(E)-6-[2-(2,4-Dichlorophenyl)ethenyl]-3,4,5,6-tetrahydro-4-hydroxy-2H-pyran-2-one Isomer B (1.1 g, 2.7 mmole) of Step G was dissolved in 95% ethanol (25 ml) containing 1 N sodium hydroxide (5.4 ml, 5.4 mmole) and the solution was refluxed for 18 hours. The ethanol was removed in vacuo and the residue was suspended in water (100 ml) and acidified with 6 N hydrochloric acid. This aqueous mixture was extracted with ether (2×100 ml). The ether extracts were combined, washed with brine (3×50 ml), dried over magnesium sulfate and filtered. The filtrate was evaporated in vacuo leaving the intermediate acid as a yellow oil (0.85 g).

A solution of the yellow oil in toluene (150 ml) was refluxed through a soxhlet containing molecular sieves (3 A) for 5 hours. The solution was evaporated in vacuo leaving the (−)-trans isomer as a yellow solid. The compound was recrystallized twice from n-butyl chloride to give white needles (0.34 g, 44%) melting at 114°–115° C., pmr (CDCl$_3$) δ2.03 (2H, m), 2.73 (2H, m), 4.46 (1H, m), 5.41 (1H, m), 6.19 (1H, dd), 7.01 (1H, d), 7.14–7.50 (3H, m).

Analysis Calc. for C$_{13}$H$_{12}$Cl$_2$O$_3$: Calc.: C, 54.37; H, 4.21. Found: C, 54.31; H, 4.26.

$[\alpha]_D^{25} = -6.6$ (C, 0.555, chloroform)

Preparation of (E)-trans-6-[2-(3,5-dichloro-4′-fluoro-2-[1,1′-biphenyl-yl)ethenyl]-3,4,5,6-tetrahydro-4-hydroxy-2H-pyran-2-one Step A. Preparation of 2,4-dichloro-6-methoxybenzaldehyde By substituting an equimolar amount of methyl iodide for benzyl bromide in Step A of the first preparation there was obtained a corresponding amount of the title compound as a white powder, mp 110°–111° C.

Step B. Preparation of N-(2-Hydroxy-1,1-dimethylethyl)-2,4-dichloro-6-methoxybenzamide A suspension of 2,4-dichloro-6-methoxybenzaldehyde (3 g, 15 mmol) and N-bromosuccinimide (3.6 g, 20 mmol) in carbon tetrachloride (30 ml) was illuminated with a 150 W flood lamp under nitrogen with vigorous stirring on a steam bath for seven minutes. The cloudy mixture was cooled to 0° C., diluted with methylene chloride (30 ml) and treated dropwise with a solution of 2-amino-2-methylpropanol (3 ml, 30 mmol) in methylene chloride (30 ml). The ice bath was removed and the mixture was stirred at 20° C. for twenty hours.

The reaction mixture was filtered and the collected solids were washed with additional methylene chloride (50 ml). The clear filtrates were combined and washed with H$_2$O (100 ml), 5% HCl (100 ml), 5% NaOH (100 ml), H$_2$O (100 ml) and brine, then dried (MgSO$_4$), filtered and evaporated in vacuo to provide the title compound as a white powder (3.6 g, 82%), mp 130°–132° C. Crystallization from hexane-toluene (10:8, V:V) provided an analytical sample of title compound, mp 131°–132° C.

Analysis Calc. for C$_{12}$H$_{15}$Cl$_2$NO$_3$: Calc: C, 49.33 H, 5.18 N, 4.79. Found: C, 49.51 H, 5.27 N, 4.62.

Step C. Preparation of 2-(2,4-Dichloro-6-methoxyphenyl)-4,4-dimethyl-2-oxazoline N-(2-Hydroxy-1,1-dimethylethyl)-2,4-dichloro-6-methoxybenzamide (5.5 g, 18.8 mmol) was treated dropwise with thionyl chloride (5.5 ml) and stirred magnetically at 20° C. for 30 min. Dry ether (100 ml) was added, the mixture was stirred for an additional one hour and the oxazoline hydrochloride precipitate was collected by filtration. The salt was neutralized with 20% sodium hydroxide to afford an alkaline mixture which was extracted with ether. The ethereal extract was dried (MgSO$_4$) and concentrated to give an oil (3.6 g, 70%), which crystallized on standing, mp 47°–50° C.

Analysis for C$_{12}$H$_{13}$Cl$_2$NO$_2$: Calc: C, 52.57 H, 4.78 N, 5.11. Found: C, 52.60 H, 4.98 N, 4.99.

Step D. Preparation of 2-(3,5-Dichloro-4′-fluoro-2-[1,1′-biphenyl]yl)-4,4-dimethyl-2-oxazoline 4-Fluorophenylmagnesium bromide, prepared from 4-fluorobromobenzene (120 mmol) and magnesium (120 mmol), in dry THF (75 ml) was added dropwise to a stirred solution of 2-(2,4-dichloro-6-methoxyphenyl)-4,4-dimethyl-2-oxazoline (100 mmol) in dry THF (150 ml) under N$_2$ at 20° C. Stirring of the solution was continued for 20 hours and then the reaction mixture was quenched by the addition of saturated ammonium chloride solution. The resulting mixture was extracted with ether (2×500 ml), dried over MgSO$_4$, filtered and evaporated. The residue was chromatographed on silica gel (ethyl acetatehexane) to provide title compound (85%), mp 93°–95° C.

Analysis for C$_{17}$H$_{14}$Cl$_2$FNO: Calc: C, 60.37 H, 4.17 N, 4.14. Found: C, 60.72 H, 4.17 N, 3.89.

Step E. Preparation of 2-(3,5-Dichloro-4'-fluoro-2-[1,1'-biphenyl]yl)-3,4,4-trimethyl-2-oxazolium iodide A solution of 2-(3,5-dichloro-4'-fluoro-2-[1,1'-biphenyl]yl)-4,4-dimethyl-2-oxazoline (4.6 g, 13.6 mmol) and methyl iodide (7 ml) in nitromethane (30 ml) was stirred on a steam bath for sixteen hours. The cooled reaction mixture was diluted with dry ether (200 ml) and, after cooling in an ice-bath, the crystalline product was collected to give 6 g (92%) of the title compound, mp 214°–216° C. (dec.). Crystallization from acetonitrile-ether (1:3, V:V) provided an analytical sample of the title compound, mp 218°–219.5° C. (dec.).

Analysis for C$_{18}$H$_{17}$Cl$_2$FINO: Calc: C, 45.03 H, 3.57 N, 2.92. Found: C, 44.94 H, 3.47 N, 2.83.

Step F. Preparation of 3,5-Dichloro-4'-fluoro-1,1'-biphenyl-2-carboxyaldehyde A vigorously stirred suspension of 2-(3,5-dichloro-4'-fluoro-2-[1,1'-biphenyl]yl)-3,4,4-trimethyl-2-oxazolium iodide (5.9 g, 12.3 mmol) in ethanol (50 ml) was treated portionwise with sodium borohydride (550 mg, 18 mmol). After stirring for two hours at ambient temperature the clear solution was diluted with 3 N hydrochloric acid (100 ml) and stirred on a steam bath for two hours. The reaction mixture was then cooled, diluted with H$_2$O (200 ml) and extracted with ether (300 ml). The ether extract was washed with H$_2$O (2×200 ml) and brine, then dried (MgSO$_4$), filtered and evaporated in vacuo to provide 2.72 g (82%) of the title compound, mp 66°–68° C. Crystallization from petroleum ether provided an analytical sample of the title compound, mp 73°–74° C.

Analysis for C$_{13}$H$_7$Cl$_2$FO: Calc: C, 58.02 H, 2.62. Found: C, 58.15 H, 2.52.

Step F$^1$: Alternate Preparation of 3,5-Dichloro-4'-fluoro-1,1'-biphenyl-2-carboxaldehyde

Part A. Preparation of Bis[μ-Acetato-0:0')bis-(3,5-dichloro-2-[(phenylimino)methyl]phenyl-C,N]dipalladium A mixture of N-[2,4-Dichlorophenyl)methylene] benzeneamine (2.5 g, 10 mmole) and palladium (II) acetate (2.24 g, 10 mmole) in acetic acid (50 ml) was heated at reflux for one hour with stirring. The turbid solution was filtered and the filtrate was diluted with water (300 ml) to give the title compound as a red solid (3.9 g, 94%). Crystallization from acetic acid-water (7:1, v:v) provided an analytical sample of the title compound, mp 203°–205° C.: pmr (CDCl$_3$) δ 1.73 (3H,S), 6.50 (H, d, J=1.5 Hz) 6.97 (2H, m), 7.12 (H,d, J=1.5 Hz) 7.33 (3H, m), 8.03 (H, S).

Analysis Calc. for C$_{30}$H$_{22}$Cl$_2$N$_4$O$_4$Pd$_2$: Calcd: C, 43.42 H, 2.67 N, 3.38. Found: C, 43.54 H, 2.59 N, 3.13.

Part B. Preparation of 3,5-Dichloro-4'-fluoro-1,1'-biphenyl-2-carboxyldehyde A solution of bis-[μ-(Acetato-0:0')bis-[3,5-dichloro-2-[(phenylimino)methyl]phenyl-C,N]dipalladium (8.29 g, 10 mmole) and triphenylphosphine (21.0 g, 80 mmole) in dry benzene (150 ml) was stirred for 30 minutes at ambient temperature under N$_2$. The 4-fluorophenylmagnesium bromide, prepared from 4-bromofluorobenzene (15.4 g, 88 mmole) and magnesium (1.94 g, 80 mmole) in dry ether (100 ml) under N$_2$ at ambient temperature, was added to the above solution in one portion. The resulting mixture was stirred for one hour at ambient temperature. After the addition of 6 N HCl (50 ml) with stirring for one hour, the mixture was filtered. The filtrate was diluted with ether (300 ml) and washed with brine (2×100 ml). The organic layer was refiltered to remove more yellow solid and the filtrate, washed with brine (2×100 ml), dried over MgSO$_4$, filtered and evaporated. The residue was chromatographed on a silica column (1000 g). Elution with ether-hexane (1:39, v:v, 5500 ml) provided a forerun which was discarded. Continued elution with ether-hexane (1:9, v:v, 5700 ml) gave the title compound as a yellow solid (4.5 g, 84%), mp 73°–74° C.: pmr (CDCl$_3$) δ 7.03—7.40 (5H, m), 7.53 (H, d, J=1.5 Hz), 10.13 (H,S).

Step G. Preparation of (E)-trans-6-[2-(3,5-dichloro-4'-fluoro-2-[1,1'-biphenyl]yl)ethyl]-3,4,5,6-tetrahydro-4-hydroxy-2H-pyran-2-one By substituting an equimolar amount of 3,5-dichloro-4'-fluoro-1,1'-biphenyl-2-carboxaldehyde in place of 2,4-dichloro-6-phenylmethoxybenzaldehyde in the alternate to alternate Step B, of the first preparation and then following the procedures of Step B through F, there was obtained a corresponding amount of the title compound, mp 121°–122° C.

Analysis for C$_{19}$H$_{15}$Cl$_2$FO$_3$: Calc. C, 59.86 H, 3.97. Found: C, 59.70 H, 3.97.

Step H. Preparation of (E)-cis-6-[2-(3,5-dichloro-4'-fluoro-2-[1,1'-biphenyl]yl)ethenyl]-3,4,5,6-tetrahydro-4-hydroxy-2H-pyran-2-one This cis isomer was obtained in comparable yield after crystallization from n-butyl chloride, mp 107°–108° C.

Preparation of (+)-(E)-(3R, 5S)-7-(3,5-dichloro-4'-fluoro-2-[1,1'-biphenyl]yl)-3,5-dihydroxy-6-heptenoic acid, ammonium salt

Step A. Preparation and Separation of Diastereomeric Amides

A solution of (±)-trans-(E)-6-[2-[3,5-dichloro-4'-fluoro-2-[1,1'-biphenyl]yl]ethenyl]3,4,5,6-tetrahydro4-hydroxy-2H-pyran-2-one (68 mmole) and 1-(−)-α-methylbenzylamine (16.5 g, 136 mmole) in tetrahydrofuran (350 ml) was refluxed for 20 hours. The tetrahydrofuran was removed in vacuo and the residue was stirred in ether (500 ml) and the precipitate collected to give diastereomer A which was twice stirred for 15 minutes in refluxing ether (500 ml) to yield a colorless solid (13.0 g, 36%) which melted at 128.5°–129.5° C.

Step B. Preparation of (+)-(E)-(3R, 5S)-7-[3,5-dichloro-4'-fluoro-2-[1,1'-biphenyl]yl]-3,5-dihydroxy-6-heptenoic acid, ammonium salt Diastereomer A (6.2 g, 12.3 mmole) of Step A was dissolved in 95% ethanol (600 ml) containing 1 N NaOH (60 ml, 60 mmole) and the solution was refluxed for 16 hours. The solvent was removed in vacuo and the residue was suspended in ice water (200 ml) and ether (500 ml) and subsequently acidified with 3 N HCl (50 ml). The ether layer was washed successively with ice-cold 1 N HCl (200 ml), brine (2×200 ml), dried over MgSO₄, and filtered. Anhydrous ammonia was bubbled through the cold ethereal solution for 2 minutes. Vigorous stirring was then continued at 20° C. for 1 hour and then the mixture was cooled slowly to ca 5° C. Filtration provided the title compound as tiny colorless needles (4.3 g, 84%), mp 105°–108° C. dec. pmr (d₆-DMSO) δ 1.15 (H, m), 1.41 (H, m), 1.99 (H, dd), 2.14 (H, dd), 3.66 (H, m), 4.11 (H, dd), 5.52 (H, dd) 6.38 (H, d), 7.23–7.42 (5H, m), 7.69 (H, d).

Analysis for $C_{19}H_{20}Cl_2FNO_4$: Calc: C, 54.82; H, 4.84; N, 3.36. Found: C, 55.13; H, 4.98; N, 3.07.

$[\alpha]_D^{27} = +10.75°$ (C, 1.6; water)

The following Example illustrates the novel process of this invention.

EXAMPLE 1

Preparation of trans-(E)-6-[2-(3,5-dichloro-4'-fluoro-2-[1,1'-biphenyl-]yl)ethenyl]-3,4,5,6-tetrahydro-4-hydroxy-2H-pyran-2-one A mixture of cis-(E)-6-[2-(3,5-dichloro-4'-fluoro-2-[1,1'-biphenyl]yl)ethenyl]-3,4,5,6-tetrahydro-4-hydroxy-2H-pyran-2-one (7.6 g, 20 mmole) and mercuric chloride (6 g, 22 mmole) was stirred at gentle reflux in $H_2O$—acetonitrile (1:5; V:V; 120 ml) under $N_2$ for 68 hours. The cooled reaction mixture was then diluted with $Et_2O$ (1 liter), washed with $H_2O$ (3×500 ml), and brine, dried (MgSO₄), filtered and evaporated in vacuo to provide the crude title compound (7 g) as a pale amber gum (56% cis and 44% trans by HPLC).

The residue was refluxed in toluene (100 ml) under a soxhlet fitted with 3 A sieves for 3 hours to relactonize any ring-opened diol acid present. After evaporation, the residue was chromatographed on a 60 mm, low pressure silica gel column. Elution with acetone-methylene chloride (1:5; V:V, 660 ml) gave a forerun which was discarded. Continued elution with the same eluant (640 ml) gave a cis/trans mixture of lactones as a colorless oil (5.3 g).

The cis and trans lactones were separated by chromatography on a Waters Prep LC 500. The separation was accomplished by using two prep PAK-500 silica cartridges in series and eluting with acetonemethylene chloride (1:5, V:V). Using the shave-recycle technique, 1.84 g (24%) of the title trans isomer was obtained.

The recovered cis isomer (2.7 g) may be recycled in the isomerization process.

Employing the conditions substantially as described in Example 1 but substituting for the mercuric chloride and the cis-isomer of the particular starting material used therein, any of the heavy metal salts and the cis-isomer of any of the other compounds described earlier by varying $R^1$, $R^2$ and $R^3$ there is caused a similar conversion of the cis-compound to the corresponding trans-compound.

What is claimed is:

1. A process for the preparation of the transisomer of the compound with structural formula:

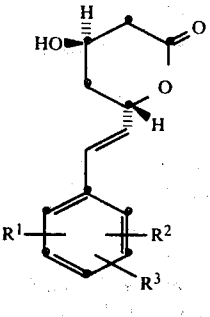

wherein
$R_1$, $R_2$ and $R_3$ are each selected from
(a) hydrogen,
(b) halogen,
(c) $C_{1-4}$ alkyl,
(d) $C_{1-4}$ haloalkyl,
(e) phenyl,
(f) phenyl substituted by
  (1) halogen,
  (2) $C_{1-4}$ alkoxy,
  (3) $C_{2-8}$ alkanoyloxy,
  (4) $C_{1-4}$ alkyl, or
  (5) $C_{1-4}$ haloalkyl, and
(g) $OR_4$ in which $R_4$ is
  (1) hydrogen,
  (2) $C_{2-8}$ alkanoyl,
  (3) benzoyl,
  (4) phenyl,
  (5) halophenyl,
  (6) phenyl $C_{1-3}$ alkyl,
  (7) $C_{1-9}$ alkyl,
  (8) cinnamyl,
  (9) $C_{1-4}$ haloalkyl,
  (10) allyl,
  (11) cycloalkyl-$C_{1-3}$ alkyl,
  (12) adamantyl-$C_{1-3}$ alkyl, or
  (13) substituted phenyl-$C_{1-3}$ alkyl in each of which the substituents are selected from
    (i) halogen,
    (ii) $C_{1-4}$ alkoxy,
    (iii) $C_{1-4}$ alkyl, or
    (iv) $C_{1-4}$ haloalkyl;

which comprises heating in an aqueous inert organic solvent in the presence of a heavy metal salt derived from a cation of a metal selected from mercury, zinc, lead, and cadmium and an anion selected from bromide, chloride, fluoride, iodide, nitrate and sulfate, the corresponding cis-isomer of structure:

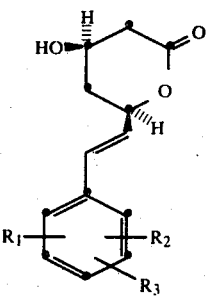

2. The process of claim 1, wherein $R_1$, $R_2$ and $R_3$ are each selected from
(a) halogen, (b) $C_{1-4}$ alkyl,
(c) $C_{1-4}$ haloalkyl,
(d) phenyl or substituted phenyl in which the substituent is
  (1) halo,
  (2) $C_{1-4}$ alkyl,
  (3) $C_{1-4}$ alkoxy, and
(e) $OR_4$ in which $R_4$ is
  (1) phenyl,
  (2) halophenyl, or
  (3) substituted phenyl-$C_{1-3}$ alkyl wherein the substituents are selected from
    (i) halogen, and
    (ii) $C_{1-4}$ haloalkyl.

3. The process of claim 1 wherein $R_1$ is in the 6-position and is halophenyloxy, halophenylalkoxy or halophenyl, where halo is fluoro or chloro; and $R_2$ and $R_3$ are halo in the 2 and 4-positions.

4. The process of claim 1 wherein $R^1$ is 6-(4-fluorophenyl) or 6-(4-(chlorophenyl) and $R^2$ and $R^3$ are 2-chloro and 4-chloro respectively.

5. The process of claims 1, 2 3 or 4 wherein the isomerization is conducted at 50°–200° C., for 40–100 hours in aqueous acetonitrile in relative volumes of 1:1 to 1:10 in the presence of mercuric chloride.

6. The process of claims 1, 2, 3 or 4 wherein the isomerization is conducted at 75°–125° C. for 60–76 hours in aqueous acetonitrile in relative volumes of 1:5 in the presence of mercuric chloride.

* * * * *